(12) United States Patent
Bellusci et al.

(10) Patent No.: US 10,415,975 B2
(45) Date of Patent: Sep. 17, 2019

(54) MOTION TRACKING WITH REDUCED ON-BODY SENSORS SET

(71) Applicant: XSENS HOLDING B.V., Enschede (NL)

(72) Inventors: Giovanni Bellusci, Hengelo (NL); Hendrick J. Luinge, Eschede (NL); Jeroen D. Hol, Hengelo (NL)

(73) Assignee: XSENS HOLDING B.V., Enschede (NL)

( * ) Notice: Subject to any disclaimer, the term of this patent is extended or adjusted under 35 U.S.C. 154(b) by 633 days.

(21) Appl. No.: 14/151,409

(22) Filed: Jan. 9, 2014

(65) Prior Publication Data

US 2015/0192413 A1 Jul. 9, 2015

(51) Int. Cl.
*G01C 21/16* (2006.01)
*A61B 5/11* (2006.01)
*G01S 11/14* (2006.01)
*G01S 13/74* (2006.01)

(52) U.S. Cl.
CPC ............ *G01C 21/16* (2013.01); *A61B 5/1114* (2013.01); *A61B 5/1123* (2013.01); *G01S 11/14* (2013.01); *G01S 13/74* (2013.01)

(58) Field of Classification Search
CPC ...... G01C 21/16; G01C 21/165; G01C 21/00; G01C 21/10; G01C 21/12; G01C 21/14; G01C 21/18; G01C 21/20; G01C 21/206; G01B 21/00; G01B 21/04; A61B 5/1123; A61B 5/1114; A61B 5/11
See application file for complete search history.

(56) References Cited

U.S. PATENT DOCUMENTS

2009/0278791 A1 11/2009 Slycke
2012/0046901 A1 2/2012 Green

FOREIGN PATENT DOCUMENTS

EP 1970005 9/2008
EP 2141632 1/2010

OTHER PUBLICATIONS

Corrales et al., Sensor Data Integration for Indoor Human Tracking, May 27, 2010, Robotics and Autonomous Systems 58, pp. 931-939.*
Zhang et al., Robust Height Tracking by Proper Accounting of Nonlinearities in an Integrated UWB/MEMS-Based-IMU/Baro System, 2012 IEEE, pp. 414-421.*
Pons-Moll et al., Outdoor Human Motion Capture Using Inverse Kinematics and von Mises-Fisher Sampling, 2011 IEEE International Conference on Computer Vision, pp. 1243-1250.*

(Continued)

*Primary Examiner* — Toan M Le
(74) *Attorney, Agent, or Firm* — McKinney Phillips LLC; Phillip M. Pippenger (57) ABSTRACT

A method of tracking the motion of a moving object having a plurality of linked segments is provided. The method uses a limited set of sensing units that are coupled to one or more of the segments to receive one or more sensor signals from the sensing units. Based on the sensor signals, the method estimates a 3D orientation and predicts a 3D position of the segments at a tracking module. The method further communicates the 3D orientation and the 3D position of the segments to a database module, and associates a pose of the object to the 3D orientation and the 3D position of the segments.

31 Claims, 6 Drawing Sheets

(56) References Cited

OTHER PUBLICATIONS

Vlasic D et al: "Practival motion capture in everyday surroundings" AMC Transactions on Graphics (TOG), ACM, US; vol. 26, No. 3; Jul. 29, 2007; pp. 35/1-35/10; ISSN: 0730-0301.
International Search Report for related International Application No. PCT/IB2015/000700; report dated Sep. 23, 2015.

* cited by examiner

MOTION TRACKING WITH REDUCED ON-BODY SENSORS SET

TECHNICAL FIELD OF THE DISCLOSURE

The present disclosure relates generally to the field of motion analysis and, more particularly, to modeling and tracking the motion of an object with linked segments using a reduced set of on-body sensors.

BACKGROUND OF THE DISCLOSURE

Various solutions currently exist for tracking the motion of objects or anatomic bodies for use in both research and commercial environments. Among others, conventional motion tracking schemes employ optical motion tracking, inertial motion tracking, tracking of on-body markers and sensors, and computer vision techniques.

In optical motion tracking, external cameras and a set of body-worn reflective markers are generally used to provide accurate motion tracking. Due to its capability of capturing motion in sub-centimeter levels of accuracy, optical motion tracking is currently used in various applications including entertainment, movie character animation, biomedical applications, and the like. However, optical motion tracking also presents several drawbacks. For example, optical motion tracking implementation typically involves high system costs, discomfort from wearing several tens of on-body markers, limitations in motion capture volume, susceptibility to occlusions and lighting conditions, and time consuming post-processing.

In inertial motion tracking, a set of inertial sensors are rigidly attached to most of the segments of a subject body, and the body pose is estimated by measuring the orientation of each segment with an attached sensor in relation to a biomechanical model. Commercially available products, such as the Xsens MVN system which employs inertial motion tracking technologies as disclosed in U.S. Pat. No. 8,165,844, uses roughly 17 sensors that are attached to the subject body. Such an approach overcomes several limitations associated with traditional optical motion tracking systems. For instance, as a substantially self-contained on-body solution, this approach provides more freedom of motion and capture volume. This approach also provides a level of accuracy that is very close to that of an optical system.

However, this solution still requires a relatively large number of body-worn sensors which not only comes with increased system costs, but can also cause undesirable obstruction especially in non-specialized applications and non-dedicated use scenarios, such as in gaming, monitoring daily life activities, and the like.

In an effort to mitigate the above-identified limitations, some recent developments have tried to achieve accurate motion tracking using a limited number of sensors or optical markers. Such solutions typically use machine learning and data-driven approaches in order to estimate the full-body pose. However, the low-dimensionality of the input measurements used presents yet other drawbacks. In one approach, relatively few (about six to nine) optical markers and two synchronized cameras are used. While this approach certainly offers a decrease in system complexity and costs, it still requires a costly external infrastructure, and further, exhibits fundamental limitations with respect to capture volume, freedom of use, occlusions as well as lighting conditions.

In another approach, relatively few inertial sensors are combined with a commercially available external acoustic positioning system. Although the number of body-worn sensors is decreased and performance is close to a conventional full-body motion capture system, the need for an external infrastructure for assessing sensor position relative to an external frame greatly limits the field and generalization during use. In yet another approach, about 4 accelerometer sensors placed on wrists and ankles are used to track motion of the subject body. Due to the low cost of the sensors and low power consumption requirements thereof, the sensors can be relatively easily integrated into bracelets, anklets, straps, or the like, and conveniently worn with minimal obstruction. However, the resulting performance is far from that desired in actual (high-fidelity) motion tracking.

In typical computer vision techniques, only a single external depth camera is used to capture the motion of the user. While this approach has the advantage of not requiring any sensors or markers to be worn by the tracked subject, there still exist obvious limitations in terms of accuracy, susceptibility to occlusions and lighting conditions, as well as capture volume. Furthermore, the tracked subject is confined within a relatively small area of space which is constrained to the location of the depth camera and the associated system. Although such limitations may be insignificant with regards to a specific application, such as in a gaming application, there are significant constraints on the overall freedom of motion which may be undesirable for use with other application types or in the more general context.

The present disclosure is directed to systems and methods that address one or more of the problems set forth above. However, it should be appreciated that the solution of any particular problem is not a limitation on the scope of this disclosure or of the attached claims except to the extent expressly noted. Additionally, the inclusion of any problem or solution in this Background section is not an indication that the problem or solution represents known prior art except as otherwise expressly noted.

SUMMARY OF THE DISCLOSURE

In accordance with one aspect of the present disclosure, a system for tracking motion of a moving object with a plurality of linked segments is provided. The system includes at least a limited set of sensing units, a tracking module and a database module. The sensing units are coupled to one or more of the segments and configured to generate sensor signals corresponding to one or more features of the segments. The tracking module is in communication with the sensing units and configured to determine a 3D orientation and a 3D position of the segments based on the sensor signals. The database module is in communication with the tracking module and configured to associate a pose of the object with the 3D orientation and the 3D position of the segments.

In accordance with another aspect of the present disclosure, a method of tracking motion of a moving object with a plurality of linked segments is provided. The method uses a limited set of sensing units that are coupled to one or more of the segments, to receive one or more sensor signals from the sensing units. The method estimates a 3D orientation and predicts a 3D position of the segments at a tracking module based on the sensor signals. The method also communicates the 3D orientation and the 3D position of the segments to a database module. The method further associates a pose of the object to the 3D orientation and the 3D position of the segments.

In accordance with yet another aspect of the present disclosure, a method of capturing motion of a moving object with a plurality of linked segments is provided. The method uses a limited set of sensing units that are coupled to one or more of the segments to receive one or more sensor signals from the sensing units. The method estimates a 3D orientation and predicts a 3D position of the segments at a tracking module based on the sensor signals. The method also corrects the 3D position of the segments at the tracking module based on the sensor signals. The method further communicates the 3D orientation and the 3D position of the segments to a database module, and associates a pose of the object to the 3D orientation and the 3D position of the segments.

Other features and advantages of the disclosed systems and principles will become apparent from reading the following detailed disclosure in conjunction with the included drawing figures.

DETAILED DESCRIPTION OF THE DISCLOSURE

Preferred embodiments of the present disclosure will be described herein below with reference to the accompanying drawings. In the following description, well-known functions or constructions are not described in detail to avoid obscuring the present disclosure in unnecessary detail. A brief overview of the system of interest will be given before presenting a detailed discussion of the various system components and functions.

Figure 1:
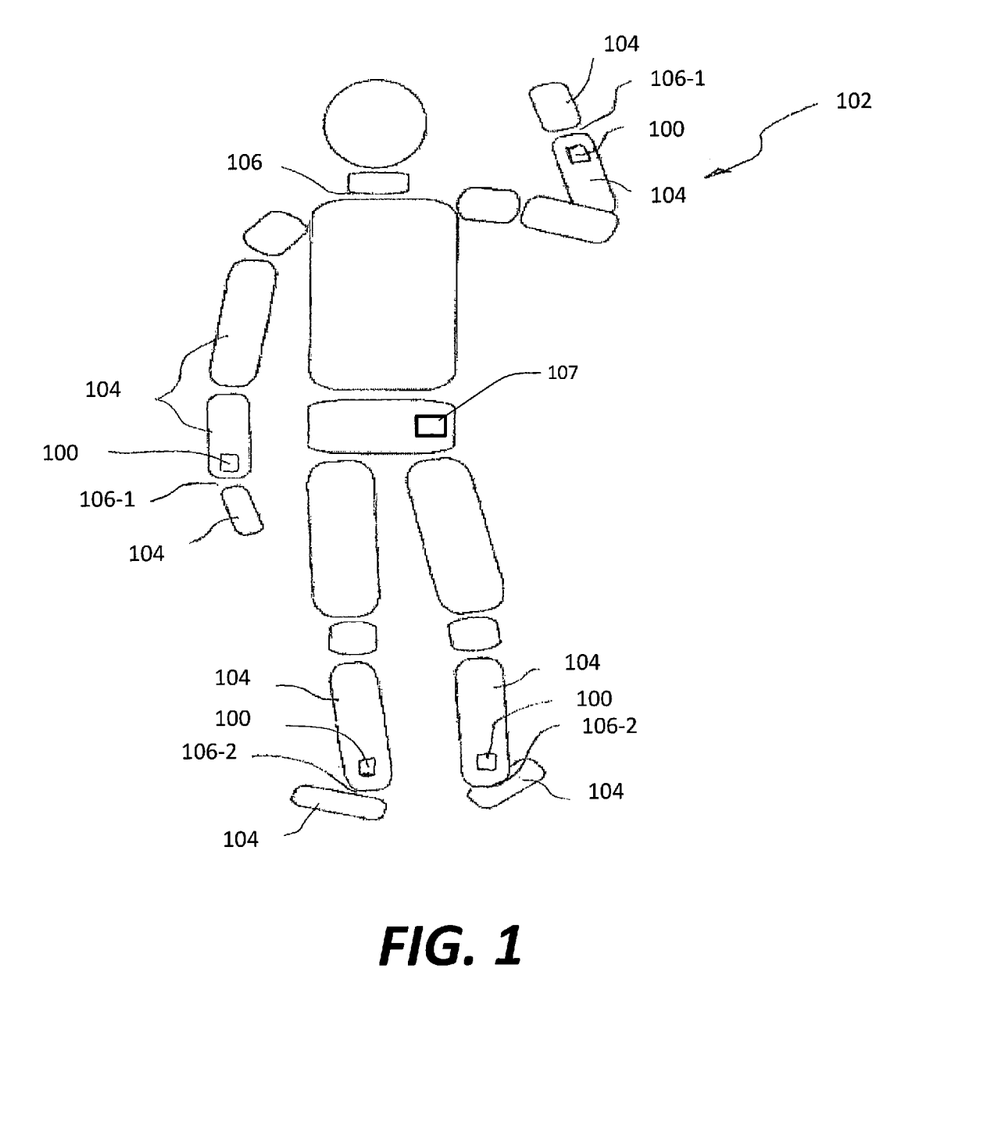
FIG. 1 is a schematic view of a model representation of a moving object that is tracked using a limited set of sensors.

Referring to FIG. 1, one example implementation of an embodiment of the present disclosure having sensing units 100 is provided in relation to a moving object, such as an anatomic body 102 having a plurality of movable segments 104 linked by joints 106. Specifically, a limited set of sensing units 100, for example, as few as approximately four on-body or body-worn sensing units 100 may be employed and coupled to one or more of the segments 104 of the tracked subject 102. In the particular embodiment shown in FIG. 1, for instance, two sensing units 100 may be attached in proximity to the wrists 106-1 while two additional sensing units 100 may be attached in proximity to the ankles 106-2 of the subject body 102. In a different embodiment, for instance a fifth sensing unit 100 may also be centrally attached to the subject body 102. It will be understood that fewer or additional sensing units 100 may be employed in similar or alternate arrangements on the body 102 or any other tracked object without departing from the scope of the appended claims.

In one embodiment, the sensing units 100 may include any one or more of 3D accelerometers, 3D gyroscopes, 3D magnetometers, and the like. In another embodiment, the sensing units 100 may alternatively or additionally include pressure sensors as well as ranging units, or means for assessing the relative ranges between the sensing units 100. In still further modifications, other combinations of suitable sensing and/or ranging units may be used. It will be understood that the embodiments disclosed herein are for exemplificative purposes only and that alternative combinations, arrangements or subsets of different sensing and/or ranging means may be used based on the desired application. Where an application involves a magnetically disturbed environment, for example, only the sensor readings from gyroscopes and accelerometers may be employed. In other modifications, the 3D accelerometers, 3D gyroscopes and 3D magnetometers, for instance, may be integrated with only a pressure sensor.

The relative range between sensing units can be obtained by means of different technologies and techniques. When using ultra-wideband (UWB) radio in a two-way-ranging operation mode, for example, a measure for the relative range between a pair of given sensing units 100 can be directly provided by the associated radio transceiver. In addition, when using acoustic signals, for example, the sensing units 100 can be synchronized (with resolutions approximately in the microseconds range) by means of dedicated radio technologies, e.g. using the wireless communication protocols as disclosed in U.S. Publication No. 2011/0109438. In such a manner, the time-of-flight (TOF) of a single transmission between an audio transmitter and an audio receiver can be immediately translated into a corresponding range, by directly multiplying the TOF by the speed of sound in air, since such nodes share a common reference clock.

Moreover, where audio signals are employed, the relatively low propagation speed of sound typically does not allow for significantly more range transmissions per second, thereby facilitating ranging between nodes that are synchronized according to a common reference clock. In particular, only a single broadcast or transmission may be necessary to provide a range estimate between the transmitter node and a plurality of receiver nodes as opposed to two-way-ranging operations in which a pair of transmissions between two nodes provides only a single range estimate. Rather, where radio signals are employed, for instance, using a UWB transceiver, the relevant packet duration can be as low as approximately 170 microseconds, and thereby potentially allow for high rates of ranging updates between all of a given set of body-worn sensing units 100. FIG. 1 also shows a tracking module 107, in the specific example implemented on a smartphone device worn by the user. In different embodiments, the tracking module might alternatively be implemented on a tablet, a personal computer, or a console game device located on the user body or in close proximity thereto. Example implementation and functionalities of the tracking module will become evident in the following.

Figure 2:
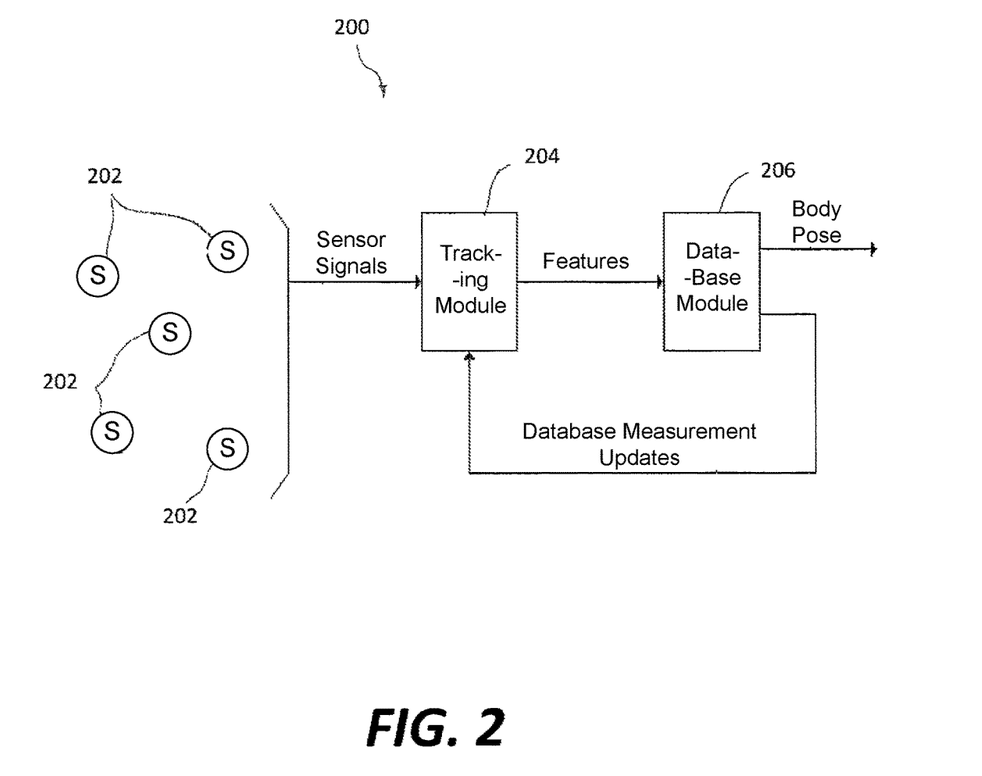
FIG. 2 is a schematic view of one example motion tracking system constructed in accordance with the disclosed principles.

Turning now to FIG. 2, one example embodiment of a system 200 for tracking motion of a moving object, such as the anatomic body 102 of FIG. 1 having a plurality of linked segments 104, is schematically disclosed. The motion tracking system 200 may generally include a set of sensing units 202, a tracking module 204 and a database module 206. As shown, the system 200 may employ a limited number of sensing units 202, each of which may be attached to a corresponding segment 104 and/or joint 106, such as the wrists 106-1 and ankles 106-2 of the subject body 102 of FIG. 1 for example. Moreover, the sensing units 202 may include any suitable combination of 3D accelerometers, 3D gyroscopes, 3D magnetometers, and any other sensing means for measuring a desired parameter of the corresponding segment 104 and/or joint 106. Alternative combinations and arrangements of the sensing units 202 will be apparent to those skilled in the art.

The sensing units 202 of FIG. 2 may be configured to generate sensor signals that are indicative of the pose, orientation, motion, position, velocity, acceleration, angular velocity, proximity, and/or any other relevant parameter of the corresponding segments 104. As shown, the sensor signals may further be communicated via wired and/or wireless means to the tracking module 204. Based on the received sensor signals, the tracking module 204 may generally determine the orientations of the tracked segments 104, as well as calculate new positions or corresponding changes in the positions of the tracked segments 104. The tracking module 204 may additionally communicate the tracked parameters or features, such as the orientations and predicted positions of the segments 104, to the database module 206. In response, the database module 206 may associate a full pose of the tracked object 102 to the features provided by the tracking module 204, and output information pertaining to the resulting pose of the object 102 for the given iteration. The database module 206 may further communicate the pose information back to the tracking module 204 as feedback upon which the tracking module 204 may rely as reference or as means for correcting subsequent iterations.

Furthermore, although the database module 206 of FIG. 2 is illustrated as a separate component within the motion tracking system 200, it will be understood that such distinctions are presented for descriptive purposes only and that practical implementations may vary. For example, in one embodiment, the database module 206 may be incorporated within a body-worn arrangement, either in a centralized fashion (e.g., provided within a smartphone in the user's possession or within one of the sensing units 202 used by the tracking module 204), or in a distributed fashion (e.g., located within each or several of the sensing units 202). In another embodiment, the database module 206 may be situated in a physically separate location but in relatively close proximity to the body-worn arrangement, for example, within a computer, tablet, console game hardware, or the like. In yet another embodiment, the database module 206 may be remotely located with respect to the body-worn arrangement, for example, in the form of a centralized, global database to which multiple authorized users or groups thereof may have dynamic access. In one such arrangement, the tracking module 204 may communicate with the global database throughout a motion capture session, for example, via WiFi, LTE, or any other suitable communication protocol. In another such arrangement, relevant portions of the global database may be downloaded at the beginning of a motion tracking session and used to generate a local database that is accessible by the tracking module 204 throughout the session. The local database may be generated, for example, according to user-specific parameters (e.g., body-dimensions, level of training, or the like), and/or according to specific actions or motions to be tracked (e.g., walking, running, sporting, gaming, or the like). Information pertaining to specific actions or motions may be input directly by the user, or provided by relevant classification algorithms. In one embodiment, the database is generated in a dedicated offline training phase. In a different embodiment, the database can be dynamically augmented according to specific user characteristics of motion, for example by means of known in art unsupervised learning algorithms.

In the particular example of FIG. 2, the tracking module 102 may apply sensor fusion techniques to the sensor signals provided by the sensing units 202 to obtain an orientation $q_k^n$ of the n-th sensing unit 202 (with n being between 1 and N, and N being the total number of sensing units 202 in use) at k-th sample time, expressed in relation to a local reference frame as defined, for instance, by gravity and magnetic North from a given geographical location. A new position $p_k^n$ of each sensing unit 202, with respect to a previous position $p_{k-1}^n$, may also be calculated by double integration of the free-acceleration, for example, based on $$p_k^n = p_{k-1}^n + Tv_{k-1}^n + \frac{T^2}{2} f_{k,L}^n \qquad (1)$$

where bold symbols denote vectors, T is the update interval, $v_k^n$ is the velocity, and $f_{k,L}^n$ is the free acceleration of the n-th sensing unit 202. Moreover, the velocity $v_k^n$ may be calculated based on $$v_k^n = v_{k-1}^n + Tf_{k,L}^n$$

and $f_{k,L}^n$ may be defined by $$f_{k,L}^n = q_k^n * a_k^n * (q_k^n)' + g$$

where * denotes the quaternion multiplication operation, $a_k^n$ is the sensor acceleration reading, and g is the gravity vector. The orientation, acceleration and position of each sensing unit 202 can be correlated to the orientation, acceleration and position of the respective body segment 104 by means of a rotation and translation vector, which can be estimated either in-run, or in a dedicated calibration phase. In addition, for convenience purposes, all such quantities may be expressed with respect to a reference frame that is common to the relevant body segments 104, as described more specifically below.

Still referring to the example motion tracking system 200 of FIG. 2, the parameters or features, such as the orientations $q_k^n$ and positions $p_k^n$ of the sensing units 202 determined by the tracking module 204, may be communicated to the database module 206 and used by the database module 206 to estimate a pose of the corresponding body or object 102. In particular, the database module 206 may include therein or have access to one or more entries of predefined information with which the database module 206 may compare the parameters or features of the individually tracked segments 104 supplied by the tracking module 204. For example, the entries may include one or more sets of possible body poses, such as in the form of predefined orientations of each body segment 104, scaling information, and/or any other information relevant to the tracked body 102 and/or segments 104 thereof. Moreover, the database module 206 may estimate the pose by selecting one of the predefined poses which best approximates the parameters or features provided by the tracking module 204 for a given iteration.

The database module 206 may select the best approximate pose based on any one or more of a variety of different criteria. In one implementation, for example, the database module 206 may select the pose which exhibits the least disagreement in terms of weighted distances as measured between features of the tracked segments 104 (as characterized by the tracking module 204) and features of corresponding segments 104 (as characterized within the predefined poses). Such weighted distances may be measured using, for example, Euclidean distance in the features space. In another implementation, the database module 206 may select the pose based on an average pose derived from a set of approximate poses, or poses with segments 104 exhibiting minimal disagreement in weighted distance with the corresponding tracked segments 104. In yet another implementation, prior pose selections may be used to predict or assume specific motions of the tracked object 102 or segments 104 thereof. In one such example, the database module 206 may be configured to prefer a set of predefined poses which most closely approximates a previously selected pose so as to provide an output with smoother motions or transitions between iterations. In another related example, a Markov model may be used to associate certain probabilities of transitions among poses with respect to time. For instance, the relevant state transition matrix may be obtained during the same training phase that was used to create the database of poses and possibly in conjunction with known dimensionality reduction techniques. In yet another related example, a dynamic model may be generated from a set of previously estimated or selected poses and used to predict a new pose. In alternative modifications, the motion tracking system 200 or the database module 206 may be configured according to any other suitable machine-learning technique commonly used in the relevant art.

Referring back to the tracking module 204 of FIG. 2, the relationship in (1) by which the tracking module 204 calculates a position based on free acceleration, or the double integration thereof, may provide substantially accurate results when applied to relatively short timeframes but may also be prone to drift over larger timespans. When using 3D accelerometers and 3D gyroscopes that are, for example, comprised of relatively small and inexpensive MEMS sensors, errors may generally be negligible within timeframes of approximately one second or less. Beyond such timeframes, however, significant errors may result due to collective position drift. To address this issue, the output of the database module 206 may be fed back into the tracking module 204 as illustrated in FIG. 2 for example. In particular, a given motion tracking session is confined within a set of linked segments 104, and the position estimates are effectively constrained by the model of the linked segments 104. This, not only enables potentially instantaneous accurate results, but also essentially drift-free agreement in the long term. For example, sensing units 202 placed on the wrists 106-1 of a tracked body 102 may be separated by no more than a couple of meters. For instance, the position of the sensing units 202 with respect to a reference segment 104 may be extracted from the estimated full body pose and communicated to the tracking module 204. While the accuracy of a specific pose estimate may occasionally vary (in ranges of centimeters), the feedback information still enables long-term stabilization of the integration of free acceleration with respect to position as characterized in relationship (1). For instance, the database-driven position measurement can be modeled by $$y_{p_{db},k}^n = p_k^n + e_{p_{db},k}^n$$

where $y_{p_{db},k}^n$ is the position for the n-th sensing unit 202 (e.g., provided by the true position state in addition to noise) calculated from the full body pose provided by the database module 206. Depending on the given application scenario and framework, $e_{p,k}^n$ may be assumed as uncorrelated Gaussian noise, or as a sample from more complex distributions which may be preferred for use with sensor fusion solutions other than standard Kalman filtering.

The resulting accuracy of the pose estimated by the database module 206 may be sufficient to provide high-fidelity tracking using only a limited set of sensing units 202. For example, using four or five sensing units 202, the database module 206 may achieve full body motion tracking with an error of only a few degrees in orientation and a few centimeters in position with respect to ground-truth. This is because both orientation and position sensor signals are employed as parameters or features that are input to the database module 206. Relying only on orientation-related parameters or features, for instance, may provide performance sufficient to encompass a large variety of motions. However, ambiguities in the reconstructed motion may arise during more routine motions or movements.

While the foregoing describes estimation of a body pose with respect to a reference body segment 104, other applications may desire tracking of the absolute pose of the tracked object 102 relative to an external reference frame. This can be achieved by, for example, integrating available accelerometer sensor signals within a local frame after subtracting a gravity component. Drift due to integration may be controlled based in part on any contacts made between one or more of the body segments 104 and any predetermined surroundings thereof. For instance, when contact with surroundings is detected, a zero-velocity or a position update may be applied to limit drift.

Having only a limited number of sensing units 202, it may not be possible to directly measure the dynamics of those segments 104 without an attached sensing unit 202. For example, it may be difficult to assertively detect contact between a foot segment 104 of a tracked body 102 and predetermined surroundings when sensing units 202 are only provided on the wrists 106-1 and ankles 106-2 of the tracked body 102. To mitigate such drawbacks, contact point information may be incorporated into the architectural framework such that the database module 206 contains relevant descriptions of possible contact points between the body 102 and the surroundings thereof, as in the database training or learning phase. Specific contact point parameters or features may be calculated by the tracking module 204 and similarly used by the database module 206 to provide estimates of contact occurrences. Such parameters or features may include information pertaining to any one or more of the acceleration, velocity or position of the sensing units 202, information pertaining to any one or more of the orientation, acceleration, velocity or position of the segments 104, or information pertaining to statistics related to the overall body pose (e.g., the center of mass, center of pressure, and the like.

Figure 3:
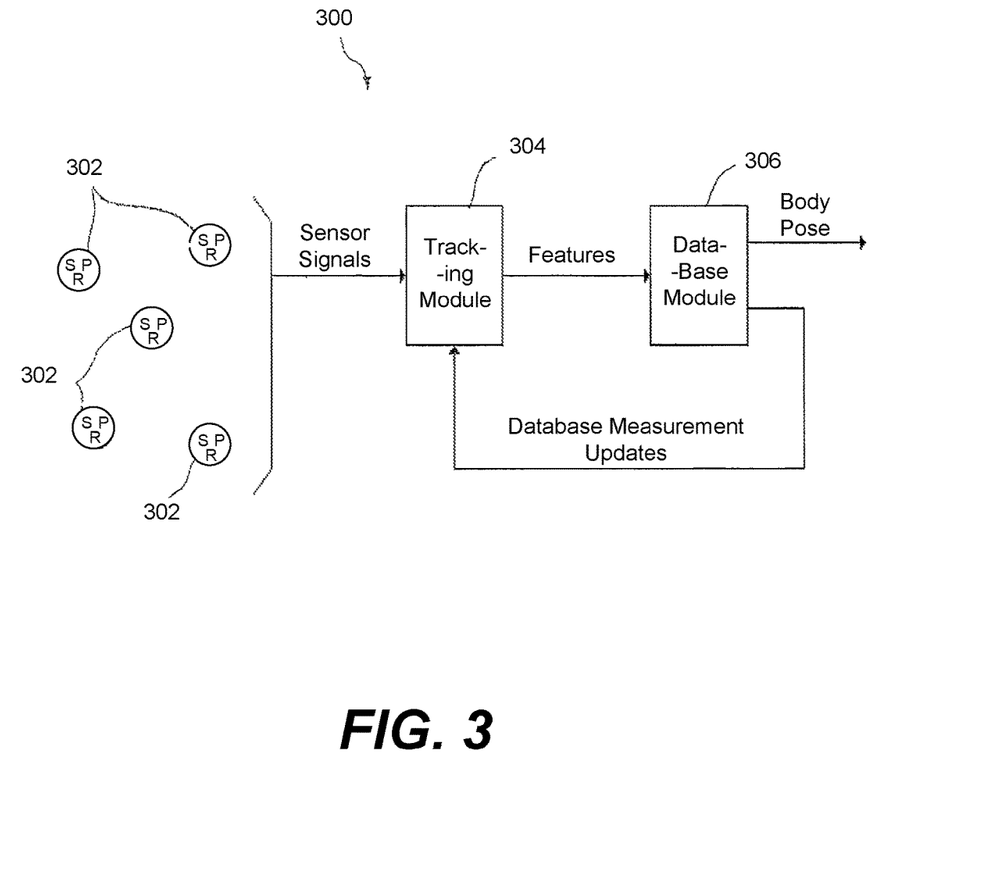
FIG. 3 is a schematic view of another example motion tracking system constructed in accordance with the disclosed principles.

Referring now to FIG. 3, another example embodiment of a system 300 for tracking motion of a moving object, such as the anatomic body 102 of FIG. 1 having a plurality of linked segments 104, is schematically provided. As in the previous embodiment, the motion tracking system 300 may generally include a limited set of sensing units 302 which communicate one or more sensor signals corresponding to various measurements of the tracked segments 104 to a tracking module 304. The tracking module 304 may calculate or estimate certain parameters or features of the tracked segments 104 and communicate the features to a database module 306 for further processing. In turn, the database module 306 may output information relating to the determined pose of the object 102 for a given iteration, and further, provide measurement updates as feedback to the tracking module 304 for use with subsequent iterations.

Similar to the embodiment of FIG. 2, the sensing units 302 in the system 300 of FIG. 3 may include any suitable combination of 3D accelerometers, 3D gyroscopes and 3D magnetometers for measuring a desired parameter or feature of the corresponding segment 104 and/or joint 106 of the tracked subject body 102. For improved accuracy, stability and overall tracking performance, the sensing units 302 may further incorporate therein pressure sensors or pressure sensing means, as well as ranging units or ranging means capable of providing a direct or derivative measure of relative ranges between sensing units 302. More particularly, a pressure sensor can provide a means for measuring the height of the corresponding sensing unit 302 using, for example, the pressure-to-height relationship $$h = c_1 \left(1 - \left(\frac{b}{b_0}\right)^{c_2}\right)$$

where b is the pressure sensor reading, h is the corresponding height estimate, $b_0$ is a reference pressure value, and $c_1$ and $c_2$ are constants. While the height estimate h may be susceptible to variations in atmospheric conditions as well as noise and other biases, the height estimate h can still be reliably used in practice for measuring the relative height between a sensing unit 302 and a reference provided that appropriate preliminary calibrations have been performed. For instance, the height of a particular sensing unit 302 may be estimated relative to another sensing unit 302 of the same body-worn arrangement, or relative to an external reference located in close proximity of the body-worn arrangement. Furthermore, the mode or reference that is selected may affect the number of calculations and measurements that are necessary. In addition, the resolution of a typical pressure sensor may be relatively large, for example, in decimeter ranges or more, and thereby potentially susceptible to outliers. Accordingly, rather than using the height estimate as a direct feature to be communicated to the database module 306, the height estimate may be better used as a measurement update so as to limit the integration drift in relationship (1). For instance, the height measurement for the n-th sensing unit 302 $y_{h_b,k}^n$ can be modeled by $$y_{h_b,k}^n = p(3)_k^n + e_{h_b,k}^n$$

i.e. it is given by the true height state in addition to noise. In one embodiment, relative ranges between sensing units 302 may be provided, for example, by means of UWB radio or acoustic signals. Depending on the specific technology used and other implementation details, the update rates may approximately reside within Hz and hundreds of Hz ranges and the typical resolution may be within centimeter and decimeter ranges. In one implementation, a relatively loosely-coupled framework or approach may exist in which the set of relative ranges $r^{m,n}$ between generic nodes m and n may be used to estimate the relative positions of the sensing units 302. The relative positions of the sensing units 302 may be determined, for example, based on a non-linear least-squares expression $$\operatorname*{argmin}_p \sum_{n,m \in N} (\|p_k^n - p_k^m\|_2 - r^{n,m})^2$$

to which standard methods (e.g., the Gauss-Newton solver) may be applied. The estimated sensor node positions may then be used directly as features, or indirectly used as means for correcting the positions of the sensing units 302 calculated based on relationship (1).

However, the foregoing loosely-coupled approach may require some additional considerations. For example, the actual position of a node may not be known without first resolving a translation and a rotation, and a relatively large number of sensing units 302 with range estimates may be required in order to adequately estimate the position. Specifically, the number of unknowns to be resolved may be (N−2)*3 (after removing six unknowns which define the origin and the x-y axes from the full set of N*3 unknown position coordinates by choosing three non-collinear nodes). Based on this particular number of unknowns, approximately five or more sensing units 302 may be required to estimate node position. Additionally, in applications involving body-worn sensor arrangements where occlusion can often occur, substantially more sensing units 302 may be required to adequately compensate for outliers or signal blockage. Accordingly, the loosely-coupled approach described above may be substituted with a tightly-coupled approach to address such considerations. More specifically, each relative range, when available, may be directly used as a measurement update in the tracking module 302 of FIG. 3 based on, for instance, $$r_k^{m,n} = \|p_k^n - p_k^m\|_2 + e_{r,k}^{m,n}$$

which can be further linearized, for instance, using the Jacobian expressions $$\frac{\delta}{\delta p_k^m} = \frac{1}{r_k^{m,n}}(p_k^m - p_k^n), \quad \frac{\delta}{\delta p_k^n} = \frac{1}{r_k^{m,n}}(p_k^n - p_k^m)$$

In such a manner, even a single immediate range update can be gainfully employed, for example, to at least partially stabilize the integration of acceleration and aid in estimating the position, as in relationship (1).

It will be readily understood that while height and range updates are generally helpful, certain use cases may still hinder the stability of the overall motion tracking application. For instance, in situations where a single sensing unit 302 is blocked for a prolonged period of time in relation to other sensing units 302 (as routinely occurs in practice due to prolonged occlusion by the subject body 102), the position of the respective segment 104 within the horizontal plane of the associated framework may be unobservable and provide undesirable tracking results. In applications employing MEMS-type inertial sensors, such occlusions may potentially cause significant errors and render the results unacceptable in as little as one second of tracking time. Accordingly, the position $y_{p_{db},k}^n$ obtained from the body pose estimated by the database module 302 may be fed back to the tracking module 304 such that the position states may be further stabilized.

In one such embodiment, the distances measured between features of the tracked segments 104 and features of corresponding database segments 104 are weighted according to fixed designations. For example, a predefined percentage of the overall weight may be heuristically attributed to each class of features (e.g., orientation and position), and further, equally partitioned among all of the features within the same class.

In another related embodiment, the weights of the distances measured between features of the tracked segments 104 and features of corresponding database segments 104 are dynamically adjusted and communicated from the tracking module 304 to the database module 306. In one possible implementation, uncertainties in the orientation and position estimates, as determined by an applied sensor fusion technique for instance, may be used to control the respective weights of distances measured between the features. Accordingly, if, for example, range updates to a particular node are unavailable for a prolonged period of time, the uncertainty of the position estimate for the node will be greater and the database module 306 will attribute a smaller weight value to the corresponding position feature, thereby reducing its influence on the overall pose detection process. In yet another possible implementation, residual values resulting from position measurement updates may be employed to adjust the weighting system. For instance, if a relatively large position-based residual results upon performing a database-driven position update, this may be indicative of an inconsistent position estimate between the tracking module 304 and the database module 306. In response, the database module 306 may reduce the weight that is assigned to the corresponding position feature to reduce any adverse effects caused thereby. Also, if, for instance, a gyroscope sensor saturates, the accuracy of the orientation may be degraded for some time. Reducing the weight for the corresponding orientation feature may provide more favorable results and overall improved performance.

Figure 5:
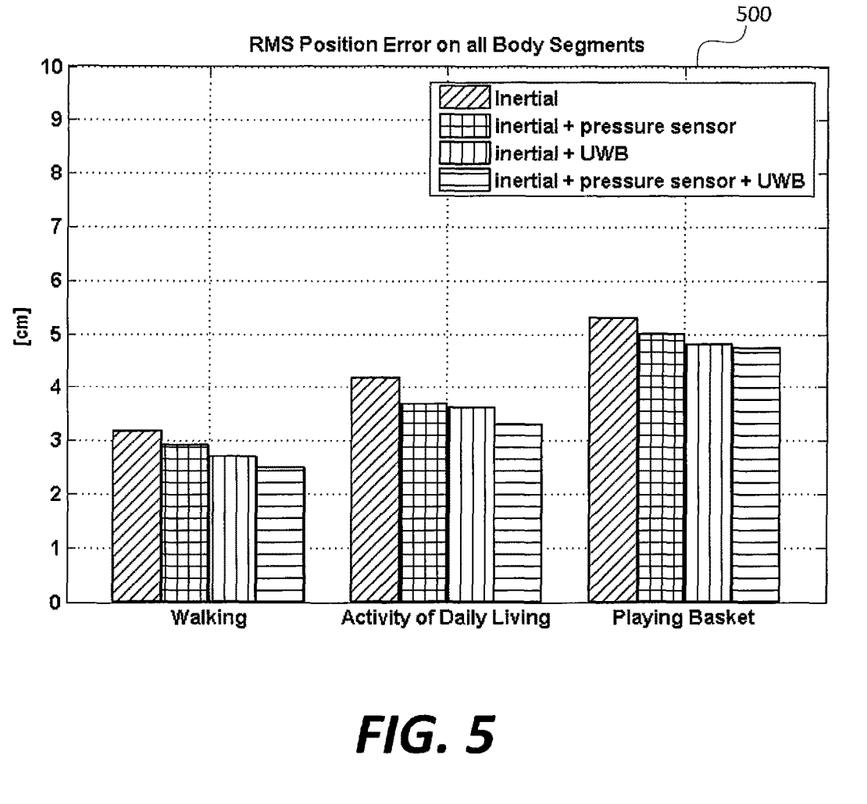
FIG. 5 is a bar plot showing the RMS full-body segments position error provided by the proposed solution for different activities and combinations of sensor types, compared to a traditional motion capture system based on 17 sensors.
Figure 6:
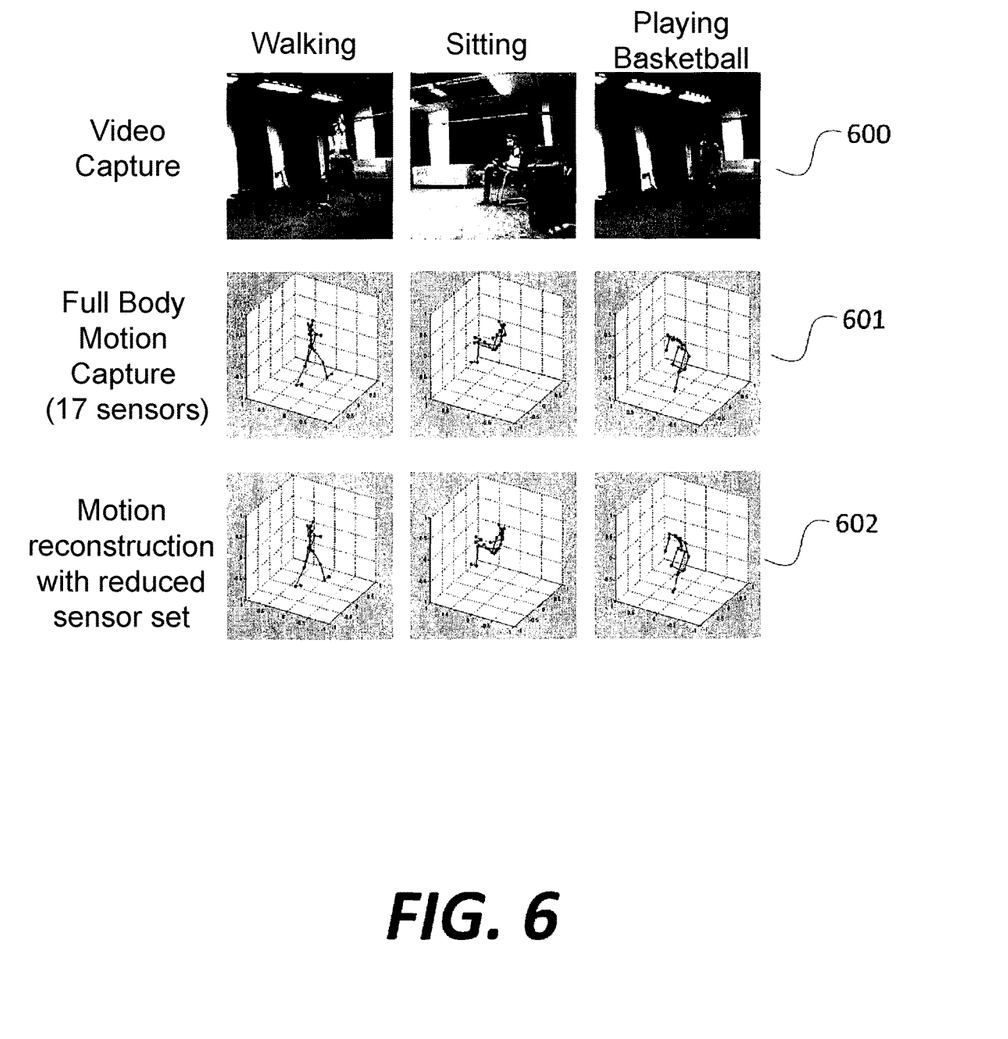
FIG. 6 shows snapshot examples for the case of video recording, the corresponding full body motion capture based on 17 sensors, and the corresponding proposed motion reconstruction with reduced sensors set, for three different motion types.

FIG. 5 shows examples of RMS full-body segment position errors which can be achieved with the disclosed system and techniques, using in this specific case 5 sensing units, for different motion types, and for different combinations of sensing modalities. The errors are evaluated versus the results provided by traditional full-body motion capture using 17 sensors. It can be appreciated that the solution is capable of providing accurate motion reconstruction results, with errors in the order of only a few centimeters in reconstructed segments position. As a further example, FIG. 6 shows snapshots examples for the case of scene video recording, full-body motion capture based on 17 sensors, and the proposed motion reconstruction with reduced sensors set, for three different motion types. Also in this case, the high level of achieved motion reconstruction fidelity is evident.

Figure 4:
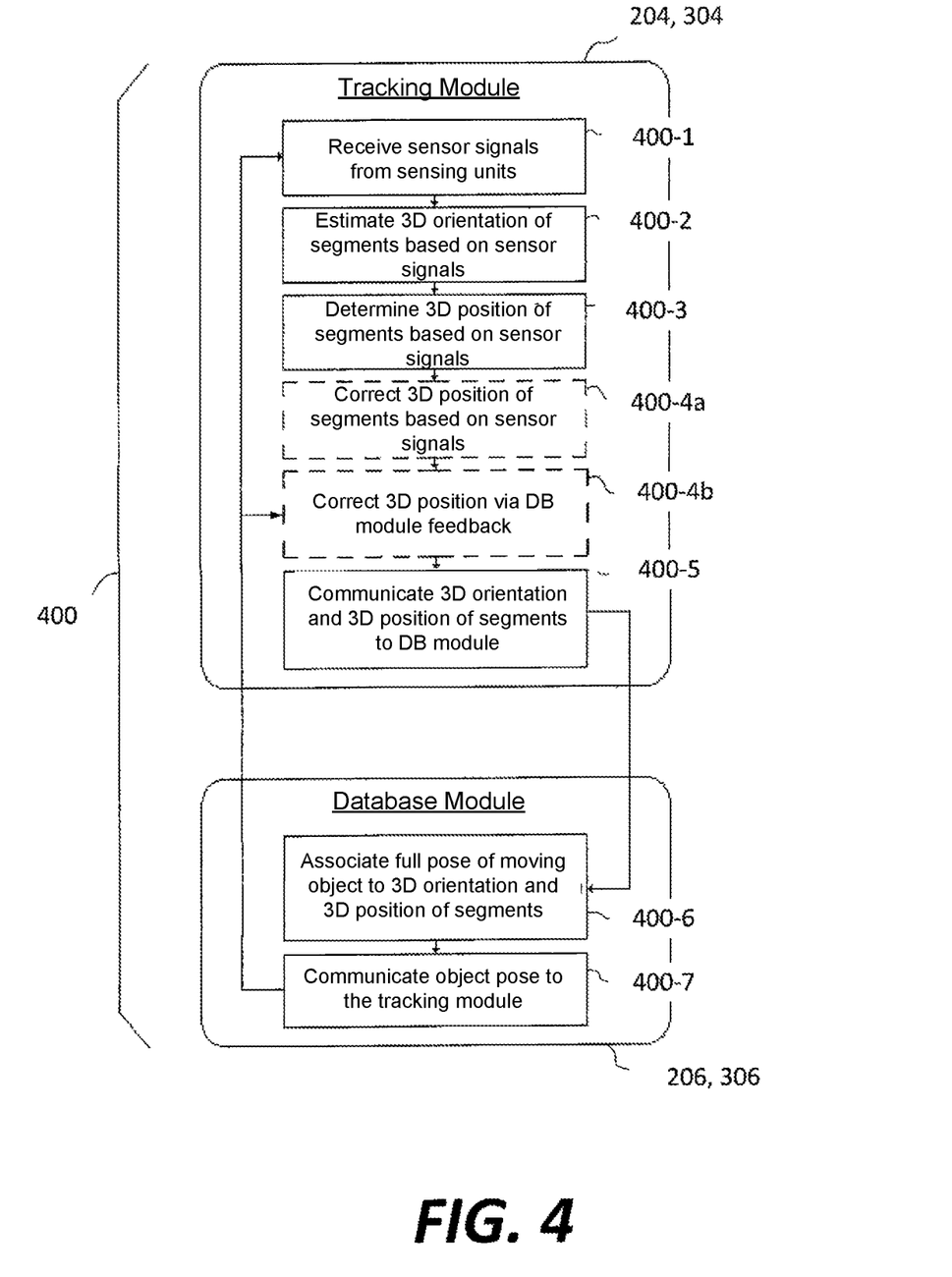
FIG. 4 is a diagrammatic view of one example algorithm or method for operating a motion tracking system constructed in accordance with the disclosed principles.

The foregoing motion tracking systems 200, 300, as well as the respective tracking modules 204, 206 and database modules 304, 306 thereof, and any variations thereof may be implemented using any combination of internal digital signal processing (DSP) circuitry disposed within the sensing units 100, 202, 302, or one or more computing devices, having a controller, microcontroller, processor, microprocessor, or the like, that is adapted or programmed to process the sensor signals and perform the functions described above, or for example, as outlined by the algorithm or method 400 of FIG. 4.

In each iteration of the method 400 generally outlined in FIG. 4, the tracking module 204, 304 may initially be configured to receive one or more of the sensor signals from the associated sensing units 100, 202, 302 in step 400-1. Based on the sensor signals, the tracking module 204, 304 may be configured to estimate the corresponding 3D orientations of the tracked segments 104 in step 400-2, and further determine the corresponding 3D positions of the tracked segments 104 in step 400-3. In an additional or an optional step 400-4a, the tracking module 204, 304 may be configured to apply any needed corrections to the calculated 3D positions of the tracked segments 104 based on the sensor signals. In step 400-4b, the tracking module 204, 304 applies corrections from the database module. Furthermore, the tracking module 204, 304 may be configured to communicate the assessed features, such as the 3D orientations and 3D positions of the tracked segments 104, to the database module 206, 306 in step 400-5 for further processing.

Upon receiving the features communicated by the tracking module 204, 304, the database module 206, 306 may be configured to associate a full pose of the subject object 102 to the 3D orientations and 3D positions of the tracked segments 104 in step 400-6. More specifically, the pose of the object 102 may be estimated based on the segment features provided by the tracking module 204, 304, and for example, selected from a database of predefined and anticipated poses of the tracked object 102, as discussed in conjunction with the foregoing embodiments. Corresponding information relating to the estimated pose of the tracked object 102 for a given iteration may then be output by the database module 206, 306 and supplied to any one or more auxiliary devices which may be in communication with the motion tracking system 200, 300. The database module 206, 306 in step 400-7 may further be configured to communicate the estimated pose of the tracked object 102 back to an input of the tracking module 204, 304, for instance, to be used as feedback or for the purposes of updating measurements in subsequent iterations. For example, the estimated pose may be communicated back to step 400-4b.

It will be appreciated that the present disclosure provides systems and methods for tracking the motion of a moving object having a plurality of linked and movable segments. While only certain embodiments have been set forth, alternatives and modifications will be apparent from the above description to those of skill in the art. These and other alternatives are considered equivalents and within the spirit and scope of this disclosure and the appended claims.

What is claimed is:

1. A system for tracking motion of a moving object having a plurality of linked segments, the system comprising:
   a limited set of sensing units coupled to a subset of the segments, the subset of segments omitting one or more segments of the object, and configured to generate sensor signals corresponding to one or more features of the segments;
   a tracking module in communication with the sensing units, the tracking module being configured to determine at least a 3D orientation and a 3D position of the segments based on the sensor signals; and
   a database module in communication with the tracking module, the database module being configured to associate a pose of the entire object including all segments of the object with the 3D orientation and the 3D position of each segment.

2. The system of claim 1, wherein the database module is configured to communicate the pose of the object associated with the 3D orientation and the 3D position of the segments to the tracking module.

3. The system of claim 1, wherein the limited set of sensing units includes one or more of a 3D accelerometer, a 3D gyroscope and a 3D magnetometer.

4. The system of claim 1, wherein the limited set of sensing units further comprises one or more atmospheric pressure sensors to provide an indication of height and ranging units, the tracking module being configured to determine a relative range between one or more pairs of the sensing units.

5. The system of claim 1, wherein the tracking module is implemented on at least one of a smartphone, a tablet, a personal computer, or a console game device located on the user body or in close proximity thereto.

6. The system of claim 1, wherein the sensing units include one or more 3D accelerometers, the tracking module being configured to predict the 3D position by performing a double integration of the sensor signals from the 3D accelerometers less a gravity component.

7. The system of claim 1, wherein the tracking module is configured to associate one or more of the 3D orientation and the 3D position with a weighted influence that is also communicated to the database module.

8. The system of claim 1, wherein the tracking module is configured to determine the 3D orientation, the 3D position and a 3D acceleration of each segment with respect to a 3D orientation, a 3D position and a 3D acceleration of a reference segment.

9. The system of claim 1, wherein the tracking module is configured to calculate additional features of the segments, and communicate the additional features to the database module to enable detection of contacts between the object and predetermined surroundings thereof, the additional features including one or more of a velocity, an acceleration and a position of one or more of the segments associated with the sensing units, the database module being configured to update one or more of a velocity measurement and a position measurement of the object based on detected contact between the object and the predetermined surroundings.

10. A method of tracking motion of a moving object having a plurality of linked segments using a limited set of sensing units coupled to one or more of the segments but not all of the segments, the method comprising:
receiving one or more sensor signals from the sensing units;
estimating a 3D orientation of the segments at a tracking module based on the sensor signals;
predicting a 3D position of the segments at the tracking module based on the sensor signals;
communicating the 3D orientation and the 3D position of the segments to a database module;
associating a pose of the object including all segments to the 3D orientation and the 3D position of the segments; and
communicating the pose of the object from the database module to the tracking module, and correcting the 3D position of the segments at the tracking module based on the pose.

11. The method of claim 10, wherein the 3D position of the segments is predicted with respect to a previously determined 3D position.

12. The method of claim 10, wherein the object is an anatomic body that is modeled as a set of linked segments constrained by joints.

13. The method of claim 10, wherein the sensing units include at least one or more of a 3D gyroscope, a 3D accelerometer and a 3D magnetic field sensor.

14. The method of claim 10, wherein the 3D orientation of the segments is calculated by sensor fusion means that is applied to the sensor signals generated by the sensing units.

15. The method of claim 10, wherein the sensing units include one or more 3D accelerometers, the 3D position of the sensing units being predicted by performing a double integration of the sensor signals generated by the 3D accelerometers less a gravity component.

16. The method of claim 10, wherein one or more of the 3D orientation and the 3D position is associated with a weighted influence, the weighted influence being communicated to the database module.

17. The method of claim 10, wherein the pose of the object is communicated from the database module to the tracking module in terms of the 3D position of the segments.

18. The method of claim 10, wherein the 3D orientation, the 3D position and a 3D acceleration of each segment are determined with respect to a 3D orientation, a 3D position and a 3D acceleration of a reference segment.

19. The method of claim 10, further comprising:
calculating additional features of the segments at the tracking module;
communicating the additional features to the database module to enable detection of contacts between the object and predetermined surroundings thereof, the additional features including one or more of a velocity, an acceleration and a position of one or more of the segments associated with the sensing units; and
updating one or more of a velocity measurement and a position measurement of the object based on detected contact between the object and the predetermined surroundings.

20. A method of capturing motion of a moving object having a plurality of linked segments using a limited set of sensing units coupled to one or more of the segments but not all of the segments, the method comprising:
receiving one or more sensor signals from the sensing units;
estimating a 3D orientation of the segments at a tracking module based on the sensor signals;
predicting a 3D position of the segments with respect to a previously determined 3D position at the tracking module based on the sensor signals;
correcting the 3D position of the segments at the tracking module based on the sensor signals;
communicating the 3D orientation and the 3D position of the segments to a database module;
associating a pose of the entire object including all segments to the 3D orientation and the 3D position of the segments; and
communicating the pose of the object from the database module to the tracking module, and correcting the 3D position of the segments at the tracking module based on the pose.

21. The method of claim 20, wherein the object is an anatomic body that is modeled as a set of linked segments constrained by joints.

22. The method of claim 20, wherein the sensing units include at least one or more of a 3D gyroscope, a 3D accelerometer, a 3D magnetic field sensor, an atmospheric pressure sensor to provide an indication of height and a ranging unit capable of at least indirectly measuring a relative range between one or more pairs of the sensing units.

23. The method of claim 20, wherein relative ranges between the sensing units are provided by means employing one of ultra-wideband (UWB) radio signals and acoustic signals.

24. The method of claim 20, wherein at least one of the sensing units includes an acoustic sensor that is synchronized using radio communication protocols.

25. The method of claim 20, wherein the 3D orientation of the segments is calculated by sensor fusion means applied to the sensor signals generated by the sensing units.

26. The method of claim 20, wherein the sensing units include one or more 3D accelerometers, the 3D position of the sensing units being predicted by performing a double integration of the sensor signals generated by the 3D accelerometers less a gravity component.

27. The method of claim 20, wherein the 3D position of the sensing units is corrected by sensor fusion means that is applied to the sensor signals generated by the sensing units.

28. The method of claim 20, wherein one or more of the 3D orientation and the 3D position is associated with a weighted influence, the weighted influence being communicated to the database module.

29. The method of claim 20, wherein the pose of the object is communicated from the database module to the tracking module in terms of the 3D position of segments.

30. The method of claim 20, wherein the 3D orientation, the 3D position and a 3D acceleration of each segment are determined with respect to a 3D orientation, a 3D position and a 3D acceleration of a reference segment.

31. The method of claim 20, further comprising:
calculating additional features of the segments at the tracking module;
communicating the additional features to the database module to enable detection of contacts between the object and predetermined surroundings thereof, the additional features including one or more of a velocity, an acceleration and a position of one or more of the segments associated with the sensing units; and
updating one or more of a velocity measurement and a position measurement of the object based on detected contact between the object and the predetermined surroundings.

* * * * *